US006867400B2

(12) United States Patent
Collins et al.

(10) Patent No.: US 6,867,400 B2
(45) Date of Patent: Mar. 15, 2005

(54) METHOD AND APPARATUS FOR CONTINUOUS FLOW MICROWAVE-ASSISTED CHEMISTRY TECHNIQUES

(75) Inventors: Michael John Collins, Charlotte, NC (US); Michael John Collins, Jr., Charlotte, NC (US); Wyatt Price Hargett, Jr., Matthews, NC (US); Edward Earl King, Charlotte, NC (US); Gary Wilbert Busse, Monroe, NC (US)

(73) Assignee: CEM Corporation, Matthews, NC (US)

( * ) Notice: Subject to any disclaimer, the term of this patent is extended or adjusted under 35 U.S.C. 154(b) by 31 days.

(21) Appl. No.: 10/064,623

(22) Filed: Jul. 31, 2002

(65) Prior Publication Data

US 2004/0020923 A1 Feb. 5, 2004

(51) Int. Cl.[7] .................................................. H05B 6/74
(52) U.S. Cl. ....................................... 219/687; 219/704
(58) Field of Search ................................ 219/687, 704, 219/696, 711, 726, 745, 746, 679; 34/393; 422/129, 186, 187, 186.29

(56) References Cited

U.S. PATENT DOCUMENTS

| 4,225,235 | A | * | 9/1980 | Anderson et al. ............ 356/316 |
| 4,427,633 | A | * | 1/1984 | Peacock et al. ................ 422/83 |
| 5,235,251 | A | * | 8/1993 | Schlie ......................... 315/112 |
| 5,313,061 | A | * | 5/1994 | Drew et al. .................. 250/281 |
| 5,387,397 | A | * | 2/1995 | Strauss et al. ............... 422/129 |
| 6,136,157 | A | | 10/2000 | Lindeberg ................ 204/157.6 |
| 6,268,596 | B1 | * | 7/2001 | Lauf et al. ................... 219/687 |
| 6,403,939 | B1 | | 6/2002 | Fagrell ........................ 219/709 |
| 6,607,920 | B2 | * | 8/2003 | Jennings et al. ............. 436/155 |
| 2002/0101310 | A1 | | 8/2002 | Jennings ...................... 333/248 |
| 2002/0102738 | A1 | | 8/2002 | Jennings ...................... 436/155 |
| 2002/0117498 | A1 | | 8/2002 | Jennings ...................... 219/686 |
| 2002/0121513 | A1 | | 9/2002 | Jennings ...................... 219/679 |

* cited by examiner

*Primary Examiner*—Quang T Van
(74) *Attorney, Agent, or Firm*—Summa & Allan, P.A.

(57) ABSTRACT

The invention is a method and associated instrument for microwave assisted chemistry. The invention includes the steps of directing a continuous flow of fluid through a microwave cavity while applying microwave radiation to the cavity and to the continuous flow of materials therein, monitoring the pressure of the fluid in the cavity; and cooling the fluid in the cavity when the pressure exceeds a predetermined setpoint pressure.

18 Claims, 14 Drawing Sheets

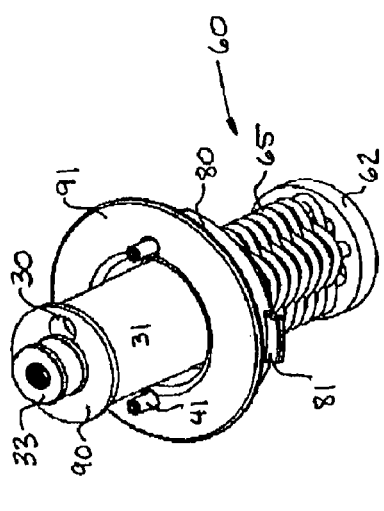
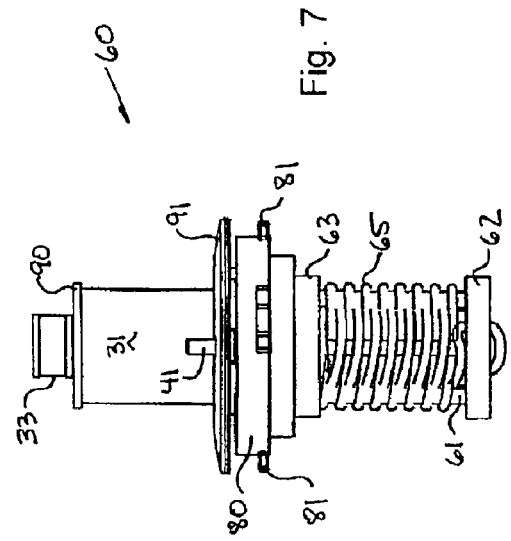

METHOD AND APPARATUS FOR CONTINUOUS FLOW MICROWAVE-ASSISTED CHEMISTRY TECHNIQUES

CROSS REFERENCE TO RELATED APPLICATIONS

This invention is related to co-pending and commonly assigned application Ser. Nos. 10/064,261 filed Jun. 26, 2002; Ser. No. 10/063,914 filed May 23, 2002; Ser. No. 10/063,628 filed May 3, 2002; Ser. No. 10/136,838 filed Apr. 19, 2002, and Ser. No. 09/773,846 filed Jan. 31, 2001. These applications are incorporated entirely herein by reference.

BACKGROUND OF THE INVENTION

The present invention relates to methods and apparatus for microwave-assisted chemistry techniques, and in particular to the use of microwaves in organic synthesis reactions. Most chemical reactions are generated, initiated, or accelerated by increasing temperature in accordance with relatively well-understood rate and thermodynamic principles. Accordingly, because microwaves can produce heat in certain qualifying substances, microwaves have been used to generate heat in a wide variety of chemical and chemistry related processes and techniques. These have typically included microwave drying for loss-on-drying moisture content analysis, and digestion of samples as a preparation step prior to other analytical techniques such as atomic absorption spectroscopy on the digested residues.

The carefully controlled conditions required for organic synthesis, however, generally have been unsuited (or vice versa) for use in typical earlier-generation microwave laboratory equipment. Specifically, although microwave devices can produce relatively large amounts of power, the nature of microwave cavities and the wavelength of microwaves tend to produce varying levels of power within the three dimensional space defined by the cavity. For large samples or samples where high temperature effects are required or desired, this aspect of microwave heating does not matter and indeed permits microwaves to work better than most other types of heating for such purposes.

Chemical synthesis, however, and in particular organic synthesis, requires a more careful and to some extent delicate application of heat to chemical reactions. In response to the need for more carefully applied microwave energy for organic synthesis purposes (by way of example and not limitation), a number of newer devices have been developed which accomplish this purpose. The apparatus and instrument set forth in the above co-pending applications are exemplary of such a device, which has gained rapid acceptance as a method for carrying out organic synthesis using microwaves. The instrument is also commercially available under the DISCOVER™ trademark of CEM Corporation, Matthews, N.C., the assignee of the present invention. The success of the DISCOVER™ instrument has led to an increase in the use of microwave synthesis techniques, and the corresponding need for additional methods of carrying out synthetic reactions in this advantageous manner.

First, in order to scale up reactions from the laboratory bench top to useful synthesis of larger amounts, it is generally advantageous to use continuous rather than batch systems. Certain reactions are also carried out more advantageously in a flowing condition because of the nature of the catalysts used. As another issue, microwave penetration of materials tends to be effective, but spatially limited; i.e. microwaves tend to penetrate part of a sample, but no further. This spatial limitation can prevent optimum utilization of microwave power in a batch content. Stated differently, the lack of penetration depth can prevent microwave irradiation from affecting an entire batch sample with the result that interior portions of the sample are merely conductively or convectionally heated by the exterior portions.

Accordingly, a flow-through system that allows greater penetration by exposing a smaller volume to microwaves at any given time can be advantageous. Yet other reactions (e.g., esterification to produce polyesters) will move to an equilibrium condition, unless one of the reaction products is removed. In the case of the esterification reaction that produces polyester, water is removed in order to prevent an equilibrium from being established between the reactives and the products, thus encouraging the production of the finished esterified polyester, rather than an equilibrium mixture of reactants and products. Continuous flow reactors can be advantageous in accomplishing such reactions.

Continuous flow reactors can also help reduce the total forces (usually pressure) that can build up in batch reactions because a proportionally smaller volume is irradiated at any given time. Additionally, the speed with which microwaves interact with responsive materials (essentially instantaneously) makes flow-through techniques at reasonable rates feasible in situations where conventional heating would be too slow to be effective.

Microwaves are generally defined as those waves falling in the portion of the electromagnetic spectrum having frequencies of from about 300 to 300,000 megahertz (MHz). The corresponding wavelengths are on the order of between about one centimeter and one meter. These are of course arbitrary limits and will be understood as such. Most common instruments that incorporate microwave radiation use a preferred assigned frequency of 2450 megahertz.

As understood by those familiar with chemical reactions exposed to microwaves, the energy of microwave photons is relatively low compared to the typical energies of chemical bonds (80–120 Kcal/mole). Accordingly microwaves do not directly affect molecular structure, but instead tend to generate molecular rotations, and by the resulting kinetic energy typically generates heat. Microwave heating does not, however, depend on the thermal conductivity of the materials being heated, and thus offers an additional advantage over typical conduction heating methods.

Because of the speed with which microwaves can heat materials, the temperature of the sample (reactants, starting materials, etc.) can quickly increase beyond a desired or advantageous temperature. Accordingly, another desired aspect of a chemistry synthesis instrument, including a microwave-assisted instrument, is the capability of controlling temperature while a reaction proceeds. Lack of temperature control can produce a number of undesired consequences. First, the temperature may increase to a point at which the reactives or the products decompose rather than react properly. Secondly, if there are volatile products being generated by the reaction, which is typical in many organic synthesis reactions, the increased pressure must be contained or released. Alternatively, the increased pressure can change the reaction kinetics in an undesired manner. Finally, an increase in temperature can also produce physical consequences to the reaction vessels and the instrument itself should pressures and temperatures and pressures become so high as to create some sort of unintended mechanical or physical failure.

Temperature control is available for microwave instruments. For example, commonly assigned U.S. Pat. No.

6,227,041 illustrates how measuring the temperature of a sample can be used to moderate (typically reducing) the applied microwave power, and thus prevent a sample from overheating and decomposing.

All chemical reactions are driven by thermodynamic factors, and most are initiated when energy is added to the reactants. In many cases, microwave irradiation can apply energy to chemical reactants faster and more efficiently than conventional heating steps. Accordingly, when the microwave power is reduced or stopped in an effort to control temperature, the efficiency of the reaction can be reduced even as heat is being produced. Thus a reaction proceeding at an elevated temperature in the absence of microwaves can still be proceeding less-efficiently than it would if microwaves were being applied.

Accordingly, co-pending and commonly assigned application Ser. No. 10/064,261 filed Jun. 26, 2002, discloses an instrument for microwave synthesis that incorporates proactive cooling in a single-mode microwave cavity. By moderating the heat generated by the applied microwaves or the reaction itself, the instrument permits a greater amount of microwave power to be applied to the reaction as may be desired or necessary.

The instrument described in the '261 application is, however, a batch-type instrument rather than a continuous-flow device.

The general attraction of continuous flow chemistry is generally well understood in concept, and a number of attempts have been made to carry it out. For example, in commonly assigned U.S. Pat. No. 5,215,715, a sample is moved in the form of a slug on a continuous basis through a microwave heated digesting system. The same or similar system is used in commonly assigned U.S. Pat. No. 5,420,039. Other recent work includes U.S. Pat. No. 6,242,723 in which two separate sets of reactants can be moved into a vessel where they can react while remaining separated by an appropriate filter while being irradiated with microwaves. U.S. Pat. No. 6,316,759 discloses an apparatus for conducting gas chromatography while heating the columns using microwaves. U.S. Pat. No. 6,303,005 shows a distillation system that uses microwave heating. U.S. Pat. No. 5,672,316 shows a semi-flow through technique that has certain proactive temperature controls, the goal of the technique being to maintain a pressure equilibrium in high-pressure reactions. U.S. Pat. No. 5,382,414 shows a reaction vessel that includes a flow-through passage for use in a conventional microwave cavity.

U.S. Pat. No. 5,387,397 shows a flow-through system that merely incorporates a "microwave enclosure" or a "suitable cavity" rather than a single mode cavity. The '397 patent also incorporates a post-irradiation cooling element. The '397 patent thus fails to recognize the power density issues raised by conventional multi-mode cavities and likewise fails to recognize that the act of reducing microwave power to control temperature can correspondingly reduce the efficient progress (rate and yield) of certain chemical reactions.

In the scientific literature, several attempts have been carried out using a conventional microwave oven (rather than a specific instrument) in which a fixed bed reactor is placed in the cavity and exposed to microwaves as the reactants flow there through. These include Plazl, AlChE journal Volume 43, Number 3, March 1997 and Pipus, Chemical Engineering Journal 76 (2000) 239–245. Other flow-through techniques have used conventional cavities as well including reports by Braun, Microporous and Mesoporous Materials 23 (1998) 79–81 and Chemat, Journal of Microwave Power and Electromagnetic Energy, Volume 33, No. 2,1998, pages 88–94.

All of these, however, use the more typical large microwave cavity that applies large amounts of power, but at a low and spatially inconsistent power density in the manner discussed above, thus making successful flow-through techniques less likely and less reproducible.

Accordingly, there remains a need for a more elegant solution to the problem of conducting sensitive organic reactions at controlled temperatures while maximizing the available use of microwave energy in a desirable manner.

SUMMARY OF INVENTION

The invention is a method of microwave-assisted chemistry comprising directing a continuous flow of fluid through a microwave cavity while applying microwave radiation to the cavity and to the continuous flow of materials therein. The method includes monitoring the pressure of the fluid in the cavity and cooling the fluid in the cavity when the pressure exceeds a predetermined set pressure. In related aspects, the pressure measurement can be used to moderate the applied power, or a temperature measurement can be used to moderate the cooling or the applied power.

In another aspect, the invention is a method of microwave-assisted chemistry that includes the steps of carrying out a chemical reaction in batch format while irradiating the reactants with microwave radiation and while concurrently externally cooling the reaction vessel to thereby identify an optimum power level and reaction time and without exceeding a temperature at which the reactants decompose or otherwise act differently than desired. The method thereafter includes the steps of directing a continuous flow of corresponding reactants through a single mode microwave cavity while applying microwave radiation to the cavity and to the continuous flow of materials therein at the power level and reaction time identified during batch format reaction of the same corresponding reactants. The method then comprises and concurrently includes externally cooling the flowing reactants while applying the microwave radiation in order to continue at the identified power level while avoiding an undesired increase in the temperature of the reaction and the reactants.

In yet another aspect, the method comprises directing a continuous flow of fluid through a single mode microwave cavity while applying microwave radiation to the cavity and to the continuous flow of materials therein and then purifying the reaction products with a scavenging composition, including scavenging combined with microwave irradiation.

In another aspect, the invention includes a method of microwave-assisted chemistry comprising the steps of directing a continuous flow of fluid through a single mode microwave cavity while applying microwave radiation to the cavity and to the continuous flow of materials therein. In the next step, the invention comprises directing the fluid from the cavity to a spectroscopic flow cell and spectroscopically evaluating the fluid, and then moderating the conditions in the cavity in response to the spectroscopic evaluation.

In its apparatus aspects, the invention comprises an instrument for microwave-assisted chemistry that includes a microwave cavity, a flow cell in the cavity, a pump for directing fluid reactants from at least one source to the flow cell, a pressure meter in fluid communication with the flow cell for measuring the pressure of fluid in the flow cell and a cooling system for cooling the flow cell in the cavity.

In another aspect, the instrument includes a microwave cavity, a flow cell in the cavity, a pump in fluid communication with the input side of the flow cell for directing fluids from a source and into the flow cell in the cavity, a spectroscopy cell external to the cavity and in fluid communication with the output side of the flow cell, and a spectrometer with the spectroscopy cell in the optical path of the spectrometer for analyzing the characteristics of the fluid flowing from the flow cell and through the spectroscopy cell.

In yet another aspect, the apparatus of the invention comprises a microwave cavity, an attenuator releasably engaged with the cavity and in microwave communication with the cavity, and a flow cell releasably engaged with the attenuator in a manner that fixes the positions of the attenuator and the flow cell with respect to one another when they are engaged and that correspondingly fixes the flow cell in the same position with respect to the cavity when the attenuator is engaged with the cavity.

The foregoing and other objects and advantages of the invention and the manner in which the same are accomplished will become clearer based on the followed detailed description taken in conjunction with the accompanying drawings in which:

BRIEF DESCRIPTION OF DRAWINGS

FIG. 6 is a perspective view of the flow cell and attenuator of the present invention.

FIG. 7 is a side elevational view of the flow cell and attenuator of FIG. 6.

DETAILED DESCRIPTION

Figure 1:
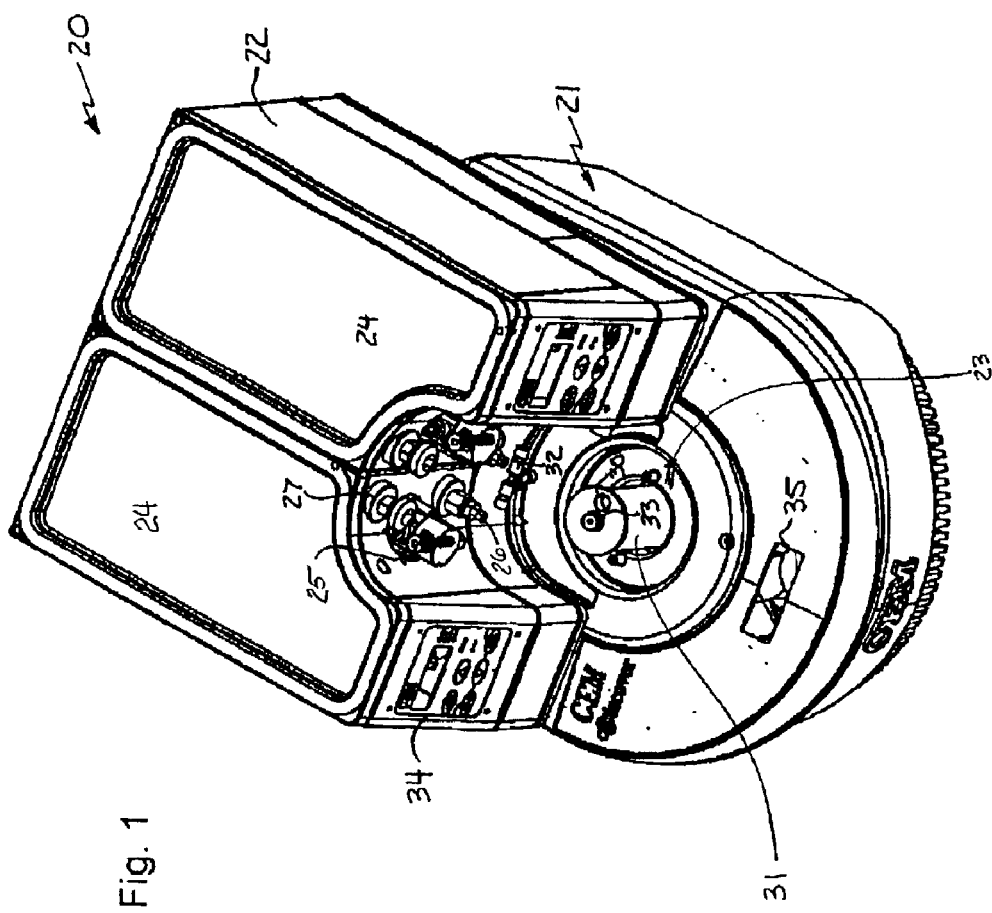
FIG. 1 is a perspective view of an instrument used in accordance with the present invention.

The invention is a method of microwave-assisted chemistry comprising directing a continuous flow of fluid through a microwave cavity while applying microwave radiation to the cavity, and to the continuous flow of materials therein. In the most preferred embodiments, the method comprises directing the continuous flow of fluid through a single-mode microwave cavity. The nature of microwave radiation and single modes is generally well understood in this art, and discussions can be found in numerous sources, including the previously incorporated patents and applications.

The invention further comprises monitoring the pressure of the fluid in the cavity. The pressure of the fluid is determined by several factors, including the pumping and flow rate, but in many circumstances, particularly organic synthesis, as reaction temperatures increase, and as reaction products are generated, potentially including gases, the pressure within a closed system will increase. Accordingly, monitoring the pressure of the fluid is one method of monitoring the progress of an ongoing chemical reaction.

In response to, or in addition to, the monitoring of the pressure, the method of the invention comprises cooling the fluid in the cavity when the pressure exceeds a predetermined set point pressure. The cooling step preferably comprises circulating or directing a coolant into and through the cavity in response to the pressure set point determination, with air being a satisfactory and preferred coolant under many circumstances. If desired, however, the step of cooling the fluid can comprise circulating a different fluid as may be convenient or necessary. In the most preferred embodiments, and as will be discussed with respect to the drawings and the apparatus aspects of the invention, the steps of directing and cooling the fluid comprise directing the fluid through a tube and then externally cooling the tube, preferably with a cooling fluid such as air, nitrogen, including nitrogen generated from liquid nitrogen, carbon dioxide, or any other appropriate gas that otherwise does not interfere with the reaction or the apparatus.

The proactive cooling step of the invention permits continued high energy transfer using the microwave irradiation, while minimizing or eliminating potentially undesired temperature-driven effects. Using the invention, very high temperatures can be reached in a "point" or "instantaneous-"sense that help drive the reaction more efficiently, but are rarely reflected in the bulk temperature of the reactants.

It will also be understood that the cooling step is not limited to a simple on-or-off context. In addition, the cooling step can include increasing or decreasing the rate of cooling at any given time in response to the measured parameters.

In preferred embodiments, the steps of monitoring and cooling the fluid comprise sending a signal representative of the pressure from a pressure monitor or detector, to a processor; i.e., a semiconductor device with both memory and logic functions. The method then includes using the processor to compare the monitored pressure to the set point pressure, and then sending a signal from the processor that initiates and runs a cavity cooling device whenever the monitored pressure exceeds the set point pressure.

In another aspect, the step of directing the fluid can comprise directing the fluid in the presence of another non-reacting material, the most common of which are catalysts. Because the catalyst is being used in the presence of microwave radiation, it (and its support in some cases) can be selected to couple with microwaves (if desired) or to be transparent to microwaves (again, if so desired).

In another aspect, the invention is a method of microwave assisted chemistry comprising carrying out a chemical reaction in batch format while irradiating the reactants with microwave radiation and while concurrently externally cooling the reaction vessel to thereby identify an optimum power level for the reaction and without exceeding a temperature at which the reactants decompose or otherwise suffer heat-related consequences different from those desired or intended. The term "reactants" is used herein in its generally understood sense to refer to those compounds or elements which react in a chemical reaction to form different compounds and elements. Nevertheless, it will be understood by those of skill in the art that the reaction can also be carried out in the presence of other materials such as reagents or catalysts while still operating within the scope of the invention.

In the present invention, once the optimum power is identified that can be applied in the presence of the available cooling, the method comprises directing a continuous flow of corresponding reactants; i.e., not the same samples, but the same chemical compositions through a single mode microwave cavity while applying microwave radiation to the cavity and to the continuous flow of materials therein at the power level identified during the batch format reaction of the same reactants. The method includes the step of cooling the flowing reactants, preferably by externally cooling the tubing through which the fluid flows in the cavity while applying the microwave radiation in order to continue at the identified and selected power level while avoiding an undesired increase in the temperature of the reaction or an undesired effect upon the reactants.

In another aspect, the invention is a method of microwave-assisted chemistry that comprises directing a continuous flow of fluid through a single-mode microwave cavity while applying microwave radiation to the cavity and to the continuous flow of materials therein, and then purifying the reaction products with a scavenging composition. In preferred embodiments, the scavenging step comprises directing the fluid through a column (or any equivalent or other satisfactory device) filled with a solid support that includes a scavenging functional group selected from the group consisting of electrophilic scavengers, nucleophilic scavengers, and combinations thereof. These terms are well understood in the art and appropriate scavengers are commercially available from a number of suppliers. In many cases, the scavenger is a microporous resin or a silica gel that supports a desired functional group. For example, a macroporous aminomethylpolystyrene resin or equivalent silica gel is suitable for a scavenger of acids or acid chlorides. In another example, a benzaldehyde-based scavenger is useful for scavenging primary amines or hydrazines and hydroxylamines. As a third example (and the selection is almost endless), macroporous resin that includes a polymer-bound ethylenediamine is useful for scavenging acids, acid chlorides, anhydrides and other electrophilic compounds. A similar set of scavenging compounds can be selected for nucleophilic scavenging, and combinations can be used where appropriate. By way of example and not limitation, such macroporous scavenger resins are available from Polymer Laboratories (Amherst, Mass.) under the StratoSpheres trademark, and scavengers based in silica gel (which are presently preferred to date) are available from SiliCycle Inc. of Quebec City, Canada. Other exemplary scavengers are available from Calbiochem-Novabiochem Corporation of San Diego, Calif., or from Sigma-Aldrich Corporation, St. Louis, Mo.

The scavenging step can remove unwanted byproducts from the reaction leading to a purified product, which, in turn, can be immediately directed to a separation step, preferably a chromatography separation step and most preferably a high pressure liquid chromatography separation step. High pressure liquid chromatography is well understood in the art and will not be otherwise discussed herein and those of ordinary skill in this art will be able to couple HPLC to the method steps in this manner without undue experimentation.

As in the previous embodiments, the method can also comprise monitoring the pressure of the fluid in the cavity and cooling the fluid when the pressure exceeds a predetermined setpoint. The temperature can also be monitored, for example, of the fluid, the ambient air in the cavity, or the external temperature of the tubing, whatever is desired or necessary, in the cavity and then the cavity can be cooled by a cooling system when the temperature exceeds a predetermined setpoint.

In another aspect, the invention is a method of microwave-assisted chemistry that comprises directing a continuous flow of fluid through a single-mode microwave cavity while applying microwave radiation to the cavity and to the continuous flow of materials therein, and then directing the fluid from the cavity to a spectroscopic flow cell and spectroscopically evaluating the fluid, and then moderating the conditions in the cavity in response to the spectroscopic evaluation. The step of directing the fluid to a spectroscopic flow cell preferably comprises directing it to an in-line cell, but can also comprise directing the fluid to a sample line separate from a main line and then evaluating the fluid in the sample line.

In preferred embodiments, the spectroscopy step is selected from the group consisting of ultraviolet, infrared, and Raman spectroscopy. Although it will be understood that the invention is not limited to these types of spectroscopy, these are quite exemplary for identification of particular molecules and compounds. As is well understood by those of ordinary skill in this art, a typical spectrometer includes a source and detector. The source directs electromagnetic radiation within a particular frequency range through the sample and then to the detector. The difference between the light emitted by the source and that collected by the detector is known as the absorbance, and the absorbance at particular frequencies identifies particular characteristics of elements and compounds. In particular, ultraviolet spectroscopy identifies electronic transitions within molecules and identifies them on that basis. Infrared spectroscopy measures asymmetric vibrational movements in molecules and identifies them correspondently, while Raman spectroscopy identifies compounds by their symmetric vibrational modes. Each of these techniques is well understood in the relevant art and need not be discussed in detail herein, and can be used in conjunction with the other elements of the invention by those of ordinary skill in this art and without undue experimentation. Furthermore, because in most circumstances the identity and nature of the reactants, the desired products, and the potential byproducts are well understood, each of these spectroscopy techniques can be extremely useful in quickly identifying such products and byproducts and potentially unreactive starting materials.

The immediate spectroscopic evaluation of the products from the continuous flow provides an excellent in-line monitoring capability because the conditions in the cavity can be quickly monitored based on the evaluations of the spectrometer. As in the previous embodiments, the preferred moderating step is to cool the cavity in response to an undesired rise in temperature which is or may be reflected by the spectroscopic results. Alternatively, the moderation can comprise adjusting the fluid flow rate through the cavity, or moderating the microwave power applied in the cavity.

In any of the embodiments of the invention, when a moderation of the microwave power is desired or necessary, a preferred technique is that set forth in commonly assigned U.S. Pat. No. 6,084,226, which explains a preferred technique for applying and adjusting continuous power in a microwave context. As set forth therein and elsewhere, the word "continuous" refers to the application of microwave power in short duty cycles so that the most efficient power level can be applied using the shortest duty cycle possible.

There are a number of apparatus aspects of the invention and these are best understood with respect to the accompanying drawings.

FIG. 1 is a perspective view of an instrument according to the present invention and broadly designated at 20. A first portion of the instrument broadly designated at 21 is a single mode focused microwave device essentially identical to the devices described and claimed in co-pending and commonly assigned application Ser. Nos. 10/064,261 filed Jun. 26, 2002; Ser. No. 10/063,914 filed May 23, 2002; Ser. No. 10/063,628 filed May 3, 2002; Ser. No. 10/136,838 filed Apr. 19, 2002, and Ser. No. 09/773,846 filed Jan. 31, 2001. The single mode cavity device 21 incorporates and integrates a modular pumping system broadly designated at 22. The nature of the modular system is such that any number of pumps can be included, and thus any number of different reactants can, be included in a given reaction scheme. In normal circumstances, between one and four pumps will be incorporated, but in each case they will be identical in concept and operation to those discussed with respect to these particular illustrations. The pumps can be any standard pump suitable for handling the reactants (and solvents or reagents) and producing the desired flow rates (e.g., 1–5 ml/min). Pumps suitable for high-pressure liquid chromatography (HPLC) are suitable for the present invention, with pumps from Scientific Systems, Inc. (State College, Pa.), being incorporated in the presently preferred embodiments The instrument 20 includes a microwave cavity in the interior portions of the instrument, and thus not entirely visible in FIG. 1, but has its location designated at 23 in FIG. 1. A flow cell (FIGS. 3–8), is present in the cavity 23. The pumps are similarly not visible in the perspective view of FIG. 1, but are carried within the pump housings 24, which, as noted above, are modular in structure and execution.

FIG. 1 does, however, illustrate the pump heads at 25 into which liquid flows from any appropriate source vessel. These can be customized vessels, or beakers, or Erlenmeyer flasks, or any other appropriate piece of laboratory glassware, or can comprise the flow from the output of another reactor or instrument. The pump outlets are illustrated at 26 and are likewise conventional in that they typically need to match to appropriate chemically inert tubing for the reactants. Each pump preferably also includes a priming and purging valve 27.

The tubing used to carry the reactants into the cavity 23 is omitted for the sake of clarity from FIG. 1, but are generally directed into an appropriate opening illustrated at 30 in FIG. 1. FIG. 1 also shows the attenuator portion 31 of the instrument 20, which, in a manner well understood in this art, prevents microwaves in the cavity from propagating outside of the instrument.

The various reactants exiting from the pump outlets are initially mixed at the T-fitting 32 which preferably also includes an appropriate filter and a relatively tortuous flow path in order to encourage the reactants to blend prior to their entry into the cavity.

Other details illustrated in FIG. 1 include a nut 33 that helps fix a portion of the attenuator 31 and flow cell together in a manner best understood with respect to the remainder of the drawings. A respective control panel 34 acts as the input/output device for each pump and includes appropriate data entry keys as well as a variety of indicators, both light emitting diodes (LEDs) and liquid crystal displays (LCDs) that display the status or operation of the instrument 20. A similar display 35 forms a portion of the single mode cavity portion 21 of the instrument 20.

Figure 2:
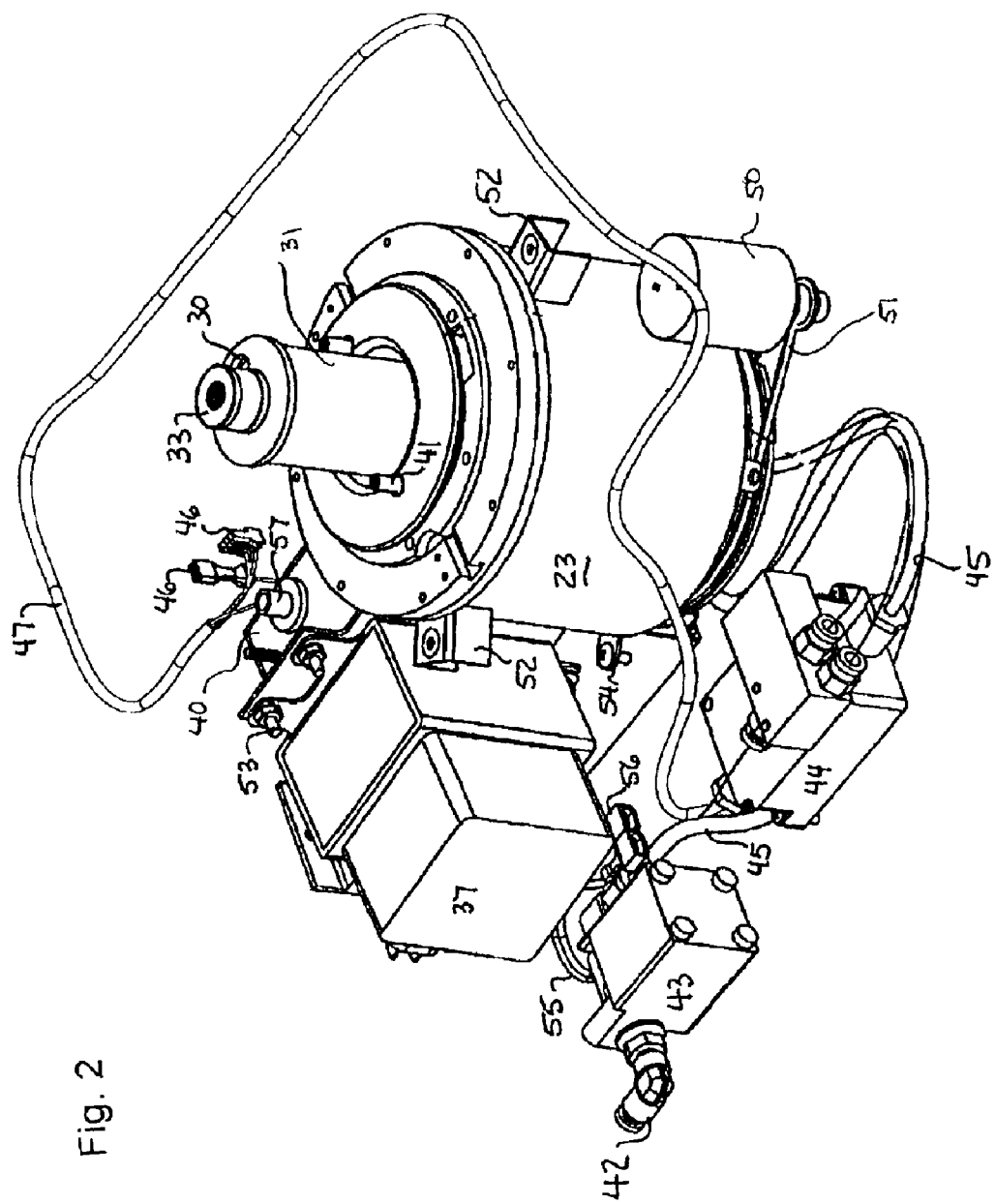
FIG. 2 is a perspective view of elements of an instrument according to the present invention including a magnetron, cavity, and attenuator.

FIG. 2 is a perspective view of portions of the instrument 20 in the absence of the housing illustrated in FIG. 1. Several of the elements are common with FIG. 1, including the cavity 23, which can now be seen as circular in shape, the attenuator 31, the inlet and outlet opening 30 for the reactant fluid tubes (not shown), and the nut 33 on the attenuator 31. Additionally, FIG. 2 illustrates that the instrument includes a microwave source 37, which in most circumstances is a magnetron, but can also comprise a klystron, or a solid-state device, such as a Gunn diode. The magnetron 37 is in microwave communication with the cavity 23, typically and preferably through the wave-guide 40. The interior of the cavity is preferably the single mode design incorporating a plurality of openings from the wave-guide, as set forth in the previously incorporated applications.

The attenuator 31 is releasably engageable with and from the cavity 23 for removing and replacing the vessel (in this case the flow cell) from the cavity 23. Typically, the attenuator engages with a ¼-turn design, best illustrated in other drawings, and FIG. 2 illustrates the handles 41 that help facilitate this task.

In preferred embodiments, the cooling system of the invention is provided by a flow of air into the cavity, it having been found convenient, appropriate, and satisfactory to use air in most circumstances. As noted earlier, however, other gases (noble gases, $CO_2$, $N_2$) including gases that have been cooled, can be used as well. Accordingly, FIG. 2 shows the airflow inlet 42 and an airflow solenoid valve 43. Because the valve 43 is a standard on and off device, the instrument typically, additionally includes an airflow regulator 44 that can variably control the flow of air to the cavity. FIG. 2 illustrates a section of tubing 45 for the airflow between the solenoid and the regulator, and also from the regulator to the cavity 23.

In preferred embodiments, the instrument includes a processor (104 in FIGS. 10 and 11) in communication with a pressure sensor 108 (FIG. 10) and the cooling system represented by the air regulator 44 and tubing 45 for moderating the cooling of the flow cell (not visible in FIG. 2) in the cavity 23, in response to the pressure measured by the pressure sensor 108. As in the case of the pumps, the pressure sensor can be the same as or similar to those conventionally used in HPLC, and such pressure sensors are available from many of the same manufacturers that provide the HPLC pumps and related equipment and components.

Figure 10:
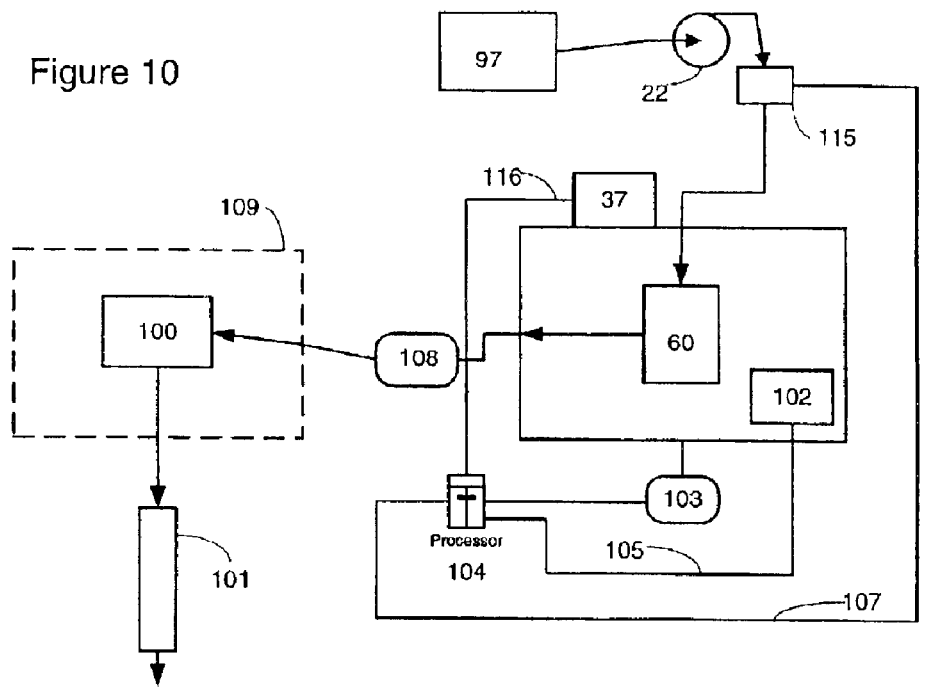
FIG. 10 is a schematic diagram of one embodiment of the instrument of the invention.
Figure 11:
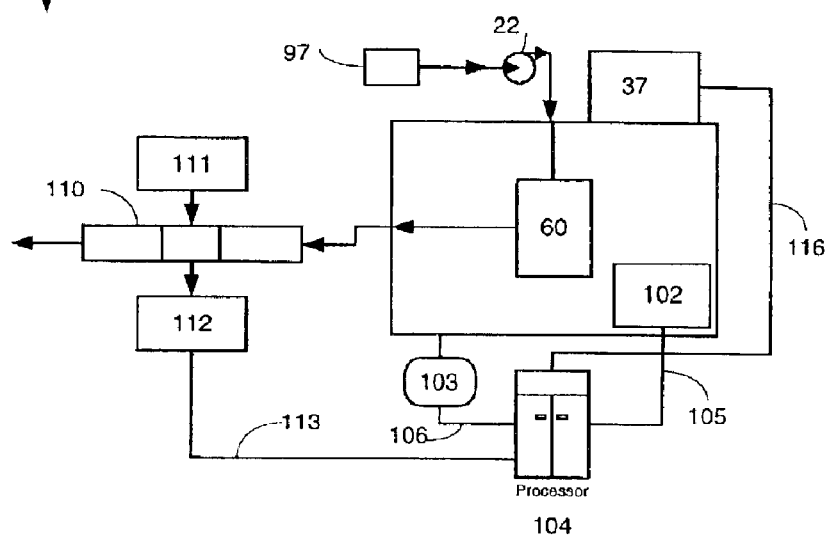
FIG. 11 is a schematic diagram illustrating another embodiment of the present invention.

Although the processor is not shown in FIG. 2, an appropriate set of plugs 46 are illustrated, and show the relative position of the processor and its accompanying board in this particular embodiment. Additionally, FIG. 2 illustrates the cabling 47 that provides the signal communication between and among the processor, the air flow regulator 44, any appropriate temperature measuring device and the power supply for the magnetron 37, all of which can be used to moderate the conditions in the cavity. With the processor in communication with the source (a magnetron 37 in this embodiment), the application of microwaves from the source can be moderated in response to the pressure detected by the pressure sensor 108, or can be moderated by the cooling system in response to the temperature measured by the temperature detector 103 (FIGS. 10–11).

FIG. 2 also shows some additional details of the illustrated instrument. These include a stirrer motor 50 and its corresponding belt 51 which can be used if desired to operate a magnetic stirrer bar (not shown) inside the cavity 23. FIG. 2 also shows a plurality of brackets 52 that help mount the cavity within the device, along with the posts 53 that are used to mount the magnetron 37 to the waveguide 40. These are basic structural features and although included in FIG. 2 for the sake of completeness, do not limit the scope of the invention or the claims. An additional bracket and screw are indicated together at 54. FIG. 2 also shows an additional set of cables 55 and plugs 56 for providing communication between the solenoid 43 and the processor. In a similar manner; the post 57 is included in this particular embodiment to provide a place where the housing of the instrument can be fixed to the portions illustrated in FIG. 2.

Figure 3:
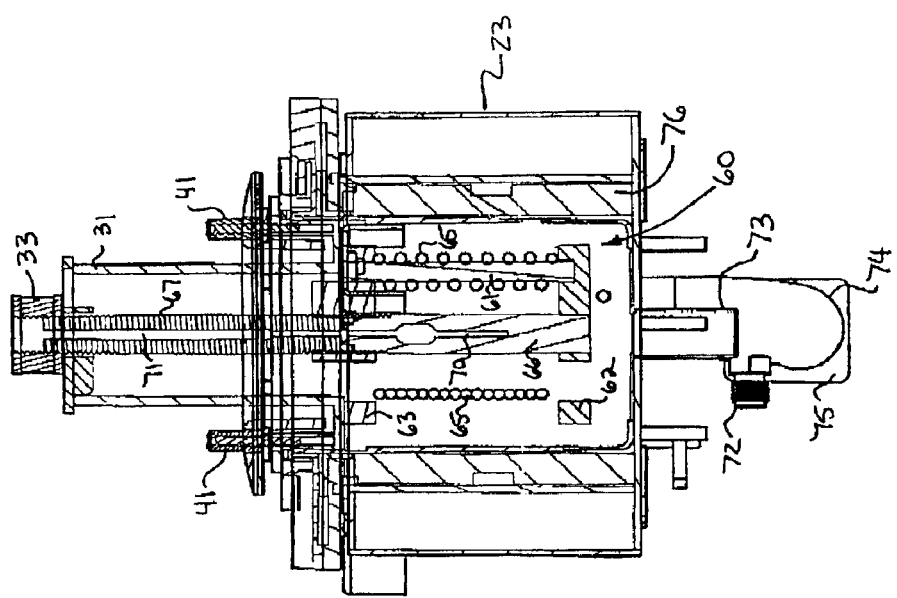
FIG. 3 is a cross sectional view of the cavity and attenuator of FIG. 2.

FIG. 3 is a cross-sectional view taken along the axis of the attenuator 31 and the cavity 23. A number of common elements from FIG. 2 are illustrated including the attenuator 31, the nut 33, the handles 41, and the cavity 23. In particular, FIG. 3 helps illustrate the advantages of the instrument in using the attenuator 31 to position the flow cell, now broadly designated at 60, at a consistent position within the cavity 23 as the attenuator 31 is releasably removed and re-engaged. FIG. 3 illustrates that the flow cell 60 includes a number of structural elements with one of the posts for this purpose being designated at 61 in FIG. 3. In preferred embodiments, (FIG. 5), the structure of the cell includes several of the posts 61, a bottom plate 62, and a top plate 63. The top plate 63 illustrated somewhat more clearly in FIG. 4 and includes a plurality of openings 64 between the posts 61.

In order to handle the fluid reactants, the flow cell 60 includes an extended length of tubing 65. The tubing 65 is illustrated in a "woven" pattern in FIGS. 3, 6, 7 and 8, or alternatively, in FIG. 3 in a more contiguous wrapping pattern as shown on the left hand side of the cross-sectional view of FIG. 3. Although the particular pattern is not crucial to the present invention, it will be understood that a consistent pattern for the tubing is similarly expected to give the most consistent results with respect to the operation of the cavity and thus, to the running of particular reactions. The tubing 65 can be made of any material that avoids interfering with the microwave field in the cavity and that is compatible with the starting materials, solvents, reagents, and expected products or byproducts. In preferred embodiments, the tubing is formed of a fluorocarbon polymer such as one of the various TEFLON™ polymers, and is wrapped in a covering (wound, woven, or braided) of fibers formed from an engineering polymer such as one of the KEVLAR® polyimides.

In order to provide the consistent positioning, the attenuator 31 is releasably engaged with the cavity 23, and the flow cell 60 and its tubing 65 are releasably engaged with the attenuator 31 in a manner that fixes the positions of the attenuator 31 and the flow cell 60 with respect to one another when they are engaged and that correspondingly fixes the flow cell 60 in the same position with respect to the cavity 23 when the attenuator 31 is engaged with the cavity 23. Stated differently, the instrument permits the flow cell 60 to be placed in a desired fixed position in the cavity 23.

In the illustrated embodiment, the positioning is accomplished with the use of a two-part (66, 67). The lower portion of the post 66 is threadedly engaged with the top plate 63 of the flow cell 60 to define a standard position, while the top portion of the post 67 is likewise threaded into the top plate 63 of the flow cell and maintained in place in the attenuator by the nut 33, previously described positioned on the top exterior surface of the attenuator 31. In the illustrated embodiment, the post portions 66 and 67 serve an axillary function in that they include respective coaxial openings (70 in post portion 66 and 71 in post portion 67). These coaxially aligned shafts 70 and 71 provide a thermal well into which an appropriate temperature measuring device can be positioned in order to measure temperature inside the cavity. The incorporation of the thermal well is not, however, necessary for the other structural aspects of the post portions 66 and 67 and the thermal well can be positioned elsewhere or the temperature measuring device can be positioned elsewhere as may be desirable or necessary.

The temperature measuring device is preferably selected to be as minimally intrusive as possible. Suitable temperature measuring devices include fiberoptic temperature sensors and transducers based on the thermal expansion of glass materials, of which representative commercial devices are available from FISO Technologies, Inc. of Quebec, Canada. Such devices offer particular advantages because they avoid interfering with, and are not affected by, microwave or radio frequency radiation. Alternatively, fiberoptic based infrared detecting thermometers such as those commercially available from LUXTRON of Santa Clara, Calif. are similarly useful. These devices direct infrared frequencies emitted by a warm sample to an appropriate photodetector via optical fibers, with the photodetector converting the measured wavelengths into a useful temperature reading.

It will also be understood that the posts 66 and 67 can be used to adjust or change the position of the tubing 65 with respect to the attenuator 31 and thus with respect to the cavity 23. It will also be understood that the illustrated structure of the flow cell 60 and the pattern of the tubing 65 are exemplary, rather than limiting, of the present invention.

Other details illustrated in FIG. 3 and the embodiment it represents include the air inlet 72 which is incorporated with the drain pipe 73. During normal operation, air from the source, solenoid and regulator described earlier, are directed into the cavity 23 through the air inlet 72 and the drain pipe 73. The drain pipe 73 serves an additional purpose, however, in that if fluid spills or leaks in the cavity 23, the drain pipe provides an available path to an appropriate spill tray. The elbow 74 illustrated in cross-section in FIG. 3 is another portion of this draining system with the drain pan not being illustrated in FIG. 3. A bracket 75 holds several of these elements in place as desired or necessary. Several of these features are also discussed in detail in the corresponding incorporated applications.

FIG. 3 also illustrates the presence of a dielectric insert 76 (e.g., formed of PTFE) which helps protect the interior of the cavity 23 and provides are additional cooling path as set forth in the incorporated applications. The remaining portions illustrated in FIG. 3, particularly the engagement between the cavity 23 and the attenuator 31 are best understood with respect to other figures.

Figure 4:
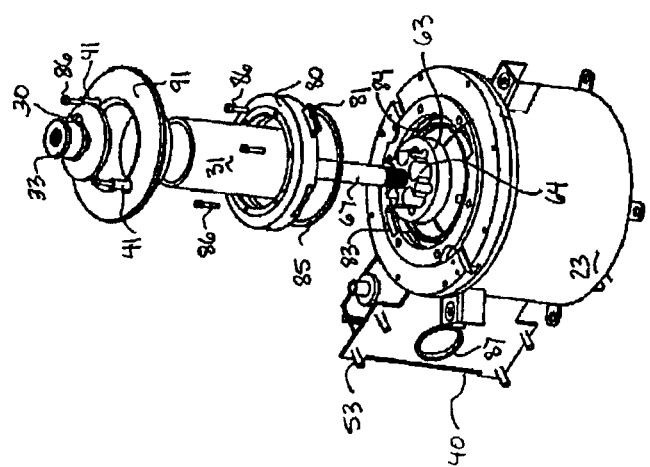
FIG. 4 is a partially exploded view of the cavity, attenuator and flow cell according to the present invention.
Figure 5:
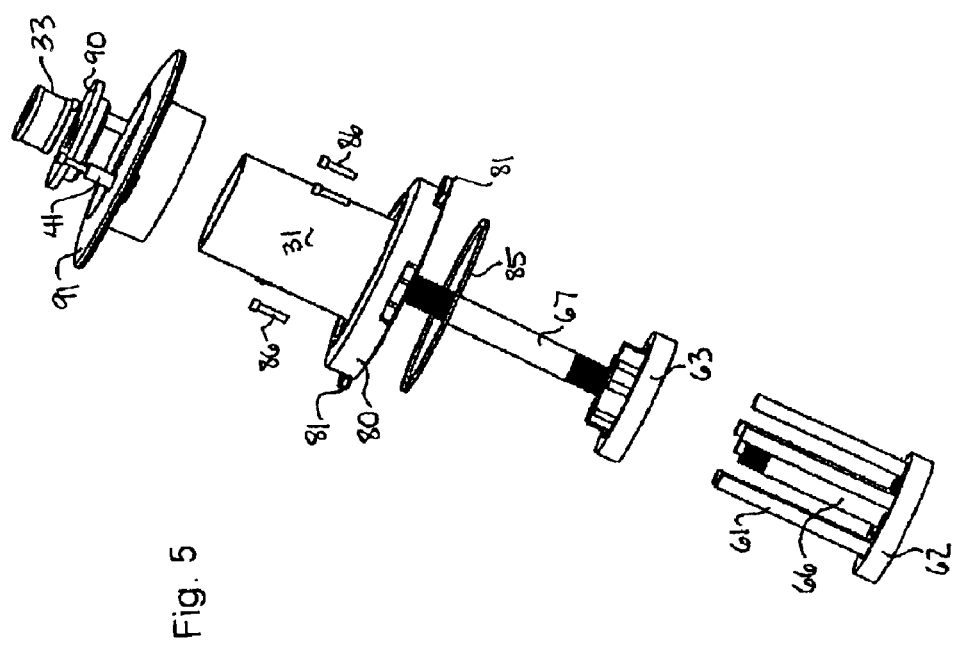
FIG. 5 is an exploded perspective view of portions of the attenuator and flow cell of the present invention.

FIGS. 4 and 5 illustrate more aspects and details of the attenuator and flow cell and their relationship to the cavity 23. FIG. 4 is a partially exploded view illustrating the attenuator 31 and portions of the flow cell 60 exploded from the cavity 23. For the sake of clarity, several of the posts 61 are eliminated from FIG. 4. In order to provide a physically and microwave secure engagement when the cavity and attenuator are engaged, the attenuator 31 is centered in a collar 80 that includes at least two radially extending locking tabs 81 (only one of which is visible in FIG. 4). The tabs 81 fit into corresponding receiving openings 83 in upper portions of the cavity 23. In order to engage the attenuator 31 and its collar 80 with the cavity, the tabs 81 are positioned in the tab receiving openings 83. Then to further secure the attenuator in place, the attenuator can be rotated approximately ¼ turn with the tabs 81 sliding in a locking channel 84 adjacent and co-planar with the lower portions of the tab receiving openings 83. As stated earlier, the handles 41 on the attenuator 31 assist in turning the attenuator 31 to either engage it or disengage it with the cavity 23. In preferred embodiments, the assembly includes the mesh ring illustrated at 85 in FIG. 4 which helps with both the mechanical and microwave sealing characteristics.

FIG. 4 also shows a few additional details such as several mounting screws or rivets 86. Because the magnetron 37 is not illustrated in FIG. 4, FIG. 4 also illustrates the opening 87 in the waveguide 40 into which the magnetron antenna (not shown) can extend to propagate the microwaves into the waveguide 40 and then into the cavity 23.

FIG. 4 also illustrates an upper cover 90 for the attenuator 31 along with an upper collar 91. The cover or cap 90 covers the entire top opening of the attenuator, with the exception of the use of the post 67, and helps prevent heat loss through the attenuator 31.

FIG. 5 shows the attenuator 31 and cell 30 in exploded fashion apart from the cavity 23. All of the elements illustrated in FIG. 5 have already been described and carry the same reference numerals as in the previous drawings and description.

FIGS. 6 and 7 are perspective and side elevational views of the attenuator 31 and flow cell 60 engaged with one another. All of the elements illustrated in FIGS. 6 and 7 have already been described previously and carry the same reference numerals as with respect to the other figures. Accordingly, FIGS. 6 and 7 provide an additional view and understanding of this aspect of the invention.

Figure 8:
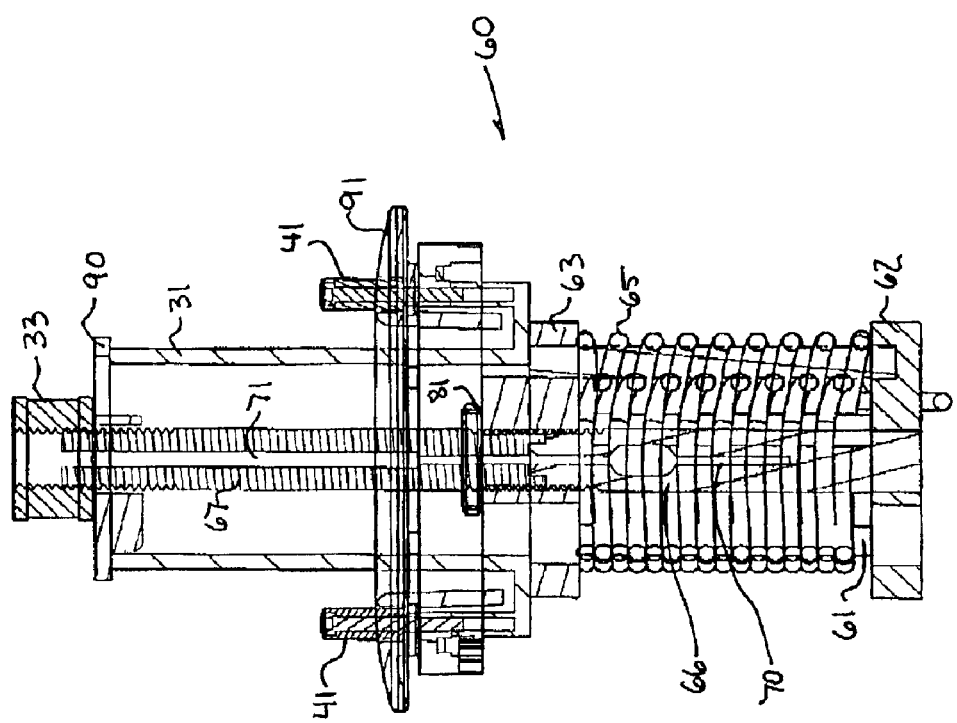
FIG. 8 is a cross sectional view of the attenuator and flow cell demonstrated in FIGS. 6 and 7.
Figure 9:
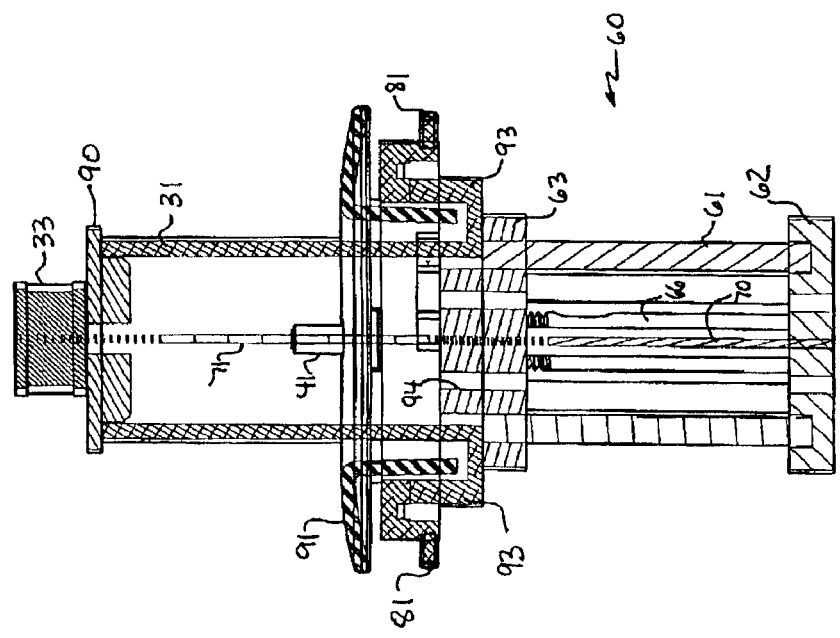
FIG. 9 is another cross sectional view of selected elements of the flow cell and attenuator.

In the same manner, FIGS. 8 and 9 are cross-sectional views, taken perpendicularly to one another, of the assembled attenuator 31 and flow cell 60. FIG. 8 illustrates the nature in which the tubing 65 can be placed around and between the posts 61 to define a flow path for fluids through the flow cell 60.

FIG. 9 illustrates a number of the same elements, but with the upper post 67 removed, and with the figure being in an orientation 90 degrees from that of FIG. 8. FIG. 9 perhaps most clearly shows the overall shape of the attenuator 31 in a proposed preferred embodiment, including the unshaped bottom portions 93. FIG. 9 also shows that the top plate 63 of the flow cell 60 defines a plurality of shafts 94 which permit the movement of air between the attenuator and the flow cell 60. The remaining elements of FIG. 9 have similarly been described with respect to previous drawings and carry the same reference numerals.

FIGS. 10 and 11 help illustrate some of the functional relationships of the elements of the instrument and the method steps of the invention. FIGS. 9 and 10 are schematic diagrams, but wherever possible, common reference numerals have been used with the other drawings.

Accordingly, FIG. 10 shows a source or vessel for reactants 97 which are drawn by the pumping system 22, then preferably through a pressure transducer 115, and delivered into the flow cell 60 in the cavity 23. From the flow cell 60 and the cavity 23, the reaction products, which will be understood to include desired products, byproducts, and in some cases unreacted starting materials, flow to and through the pressure regulator 108 following which they are scavenged in the scavenger 100. As set forth with respect to the method aspects of the claim, the scavenged products can then be immediately forwarded to a further step which in FIG. 10 is illustrated as the high-pressure liquid chromatography, 101.

The pressure regulator 108 helps maintain a constant or near-constant pressure (250 psi is typical) in the fluid so that pressure fluctuations detected by the transducer 115 can be used by the processor 104 to help moderate conditions in the cavity. The pressure regulator ("backpressure regulator") is a standard commercial device, with those available from Upchurch Scientific (Oak Harbor, Wash.) being exemplary. The backpressure regulator offers several advantages, including moderating the pressure fluctuations that can occur when gas bubbles form in the flowing fluid, and serving as a pump preload for low pressure applications.

FIG. 10 also schematically illustrates another microwave cavity 109 (dotted lines). In this regard, the scavenging step is preferably carried out under microwave irradiation either in the original cavity 23 or in a separate cavity as indicated at 109. In both cases, the use of microwaves greatly accelerates the rate of scavenging, and two specific comparative examples are included later herein.

In FIGS. 10 and 11, the cooling system is designated at 102, the temperature detector at 103, and the processor at 104. In FIG. 10 the processor is in signal communication with the cooling system 102 through the cable 105. It will be understood that a cable or wire is a presently preferred embodiment of the invention, but that any appropriate signal communication between the processor and the cooling system can be incorporated. These could include infrared communication as is common with certain computers and their peripheral devices, or communication over some other assigned frequency within the electromagnetic spectrum, or an optical cabling system as the case may be. The processor is also in signal communication with the temperature detector 103 through the cable 106 and with the pressure detector (transducer) 115 through the cable 107, and with the source 37 through the cable 116.

FIG. 11 shows a number of the same elements as FIG. 10, but in particular illustrates the spectroscopy cell 110 which is positioned external to the cavity 23 and in fluid communication with the output side of the flow cell 60. A spectrometer represented by the source 111 and detector 112 has the spectroscopy cell 110 in its optical path for analyzing the characteristics of the fluid flowing from the flow cell 60 and through the spectroscopy cell 110. The general principles and operation of spectroscopy and spectrometers are well understand in this and many related arts and will not be discussed in detail herein. The term "optical path" refers, of course, to the path defined between the source 111 and the detector 112 and does not necessarily refer to the passage of light within the visible spectrum. Indeed, as noted above, in addition to potentially using visible light spectroscopy, the invention more preferably incorporates ultraviolet spectroscopy, infrared spectroscopy, Raman spectroscopy, each which operates in frequencies and wavelengths that are outside of the visible spectrum. As in the case of FIG. 10, the processor 104 is in signal communication with the cooling system 102 through the cable 105. The processor 104 is in signal communication with the source 37 through the cable 116, with the temperature detector 103 through the cable 106, and in signal communication with the spectrometer and its detector 112 through the cable 113.

The spectroscopic evaluating step preferably comprises at least portions of the infrared spectrum of the fluid, or at least portions of the ultraviolet spectrum of the cooling fluid, or at least portions of the Raman spectrum of the flowing fluid. In each case, it will be understood that when certain reactions are being carried out, certain portions of their spectrum are well understood and can be predictably identified as present or absent. Accordingly, the spectroscopic evaluation can, but does not require, a full selection of wavelengths. It can be limited as desired or necessary to a relatively smaller range or set of ranges from which the expected products, byproducts and remaining starting materials can be identified.

With the processor and the signal communication in place, FIG. 10 illustrates how the conditions in the cavity, particularly including the operation of the microwave source 37 and the cooling system 102 can be moderated in response to the pressure detector 115 or the temperature detector 103.

The term "processor" is used herein in its generally accepted sense, and such devices are also typically referred to as microprocessors, coprocessors, or CPUs (central processing unit). Downing, Dictionary of Computer and Internet Terms, Sixth Ed. (1998), Barron's Educational Series, Inc., e.g., at pages 110, 293, and 370. As set forth therein, the processor carries out arithmetic and logical operations, and decodes and executes instructions. Processors useful for the operations described herein are commercially available, and in many cases correspond to the processors incorporated in personal computers. Such processors can also be programmed to carry out the operations described herein by those of ordinary skill in the relevant arts and without undue experimentation. In an analogous manner, FIG. 11 illustrates how the processor 104 and its relationships can moderate the conditions in the cavity 23 by moderating the microwave power from the source 37 or the operation of the cooling system 102 and in particular in response to the temperature 103 or most preferably in response to the spectrometer and particularly the detector 112.

EXPERIMENTAL

Tables 17 show some of the results of various experiments carried out using the method and apparatus of the invention, and with comparisons to prior techniques in some cases.

Tables 1 and 2 are examples of scavenging carried out under the application of microwave radiation. In the experiments carried out in Tables 1 and 2, acetonitrile was used as the solvent for the five listed compounds. These compounds were selected as having those functional groups that amine-type scavengers are designed to remove. Accordingly, Table 1 represents a scavenging reaction carried out using a silica-based amine-3 scavenger from SiliCycle Inc. (Quebec City, Canada). As the results in Table 1 show, under the influence of microwaves for four minutes, almost all of the compounds were entirely scavenged. By way of comparison, under room temperature stirring conditions i.e., a conventional scavenging technique—only three of the compounds were removed.

For the scavenging of benzoyl chloride with amine-3 scavenger, 400 mg of benzoyl chloride were used in 1 ml of solvent (acetonitrile) to form a 0.14M solution. Therefore 0.57 mmol of amine functional group constitutes 1 equivalent of scavenger. Four (4) equivalents would be 2.3 mmol of scavenger, which is 158 mg for a loading capacity of 3.6 mmol/g. The benzoyl chloride, scavenger, and solvent are added together in a 10 ml pressurized vessel and either put into the microwave system or stirred at room temperature The percent scavenged is determined by GC/MS.

TABLE 1

| Using acetonitrile | % scavenged microwave | % scavenged room temp |
|---|---|---|
| Benzoyl chloride | 100 | 100 |
| Acetic Anhydride | 99 | 99 |
| tert-butylphenylisocyanate | 100 | |
| 1,1,3,3-tetramethylbutylisocyanate | 100 | |
| benzaldehyde | 97 | 97 |
| | Amine-3 | Amine-3 |
| | 4 EQs, MW conditions | 4 EQ's, rt conditions |
| | 4 min, 150 C., 300 W | stirred 1 hr |

Table 2 represents the same experiment carried out with the same compounds, but using a triamine-3 silica based scavenger, and again comparing a microwave technique versus a conventional technique. As Table 2 indicates, microwave technique demonstrated equivalent or superior scavenging results in all cases, and was carried out in four minutes rather than one hour.

TABLE 2

| Using acetonitrile | % scavenged microwave | % scavenged room temp |
|---|---|---|
| Benzoyl chloride | 100 | 100 |
| Acetic Anhydride | 97 | 99 |
| tert-butylphenylisocyanate | 95 | 62 |
| 1,1,3,3-tetramethylbutylisocyanate | 89 | 62 |
| benzaldehyde | 80 | 59 |
| | Triamine-3 | Triamine-3 |
| | 4 EQ's, MW conditions | 4 EQ's, rt conditions |
| | 4 min, 150 C., 300 W | stirred 1 hr |

Tables 3 7 are exemplary organic synthesis reactions carried out using the flow through techniques and apparatus of the present invention. In some cases the results are shown in comparison to the identical reaction carried out in batch fashion in a manner consistent with applicant's co-pending 261 application. Unless indicated otherwise, the comparative batch reactions were carried out in a DISCOVER™ instrument from CEM Corporation, Matthews, N.C.

TABLE 3

| Knoevenagel Invention | DISCOVER ™ Instrument |
|---|---|
| 25 g malonic acid | 0.098 g malonic acid |
| 25 mL benzaldehyde | |
| 35 mL pyridine | 0.069 ml pyridine |
| 15 mL ethanol | 0.5 ml EtOH |
| FR = 1 ml/min | |
| 5 ml coil | |
| Temp = 160 C. | T = 175 C. |
| P = 250 psi | P = 250 psi |
| Power = 300 W | Pwr = 300 W |
| Cooling = 1–2 psi | Cooling = On |
| Yield = 20% | |

Figure 12:
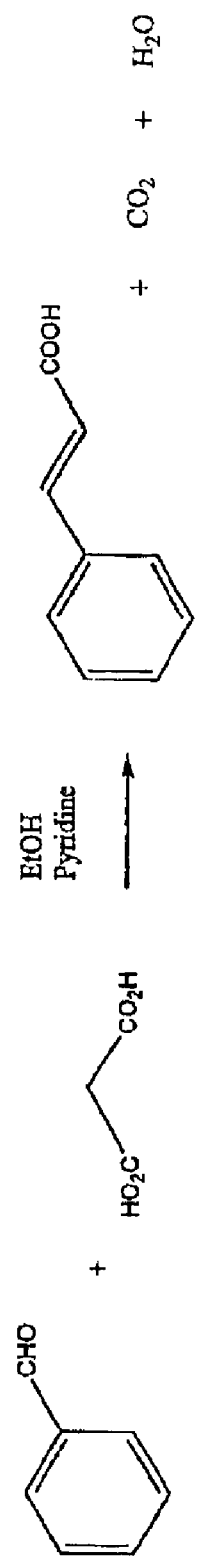
FIGS. 12 through 16 are chemical equations for exemplary reaction schemes for which the present invention has been found useful.

Table 3 shows the results of a Knoevenagel reaction (FIG. 12) using the indicated starting materials. In particular, a flow-through reaction was carried out at a flow rate of 1 milliliter per minute in a 5-milliliter coil in an instrument according to the present invention, thus defining a residence time of 5 minutes. This was compared to a batch reaction among the same compositions similarly carried out under microwave irradiation for five minutes. As Table 3 indicates, the temperature and powers used were equivalent and in the case of the invention, produced a yield of 20%, which is comparable to the results demonstrated in the prior art; e.g. U.S. Pat. No. 5,387,397.

TABLE 4

| Esterification Invention |
| --- |
| 9.1 g benzoic acid |
| 30 mL MeOH |
| 0.5 mL H2SO4 |
| FR = 1.5 ml/min |
| 5 ml coil |
| residence time = 3:20 |
| Temp = 80 C. |
| P = 250 psi |
| Power = 75 W |
| Cooling = 15 psi |
| Yield = 100% |

Figure 13:
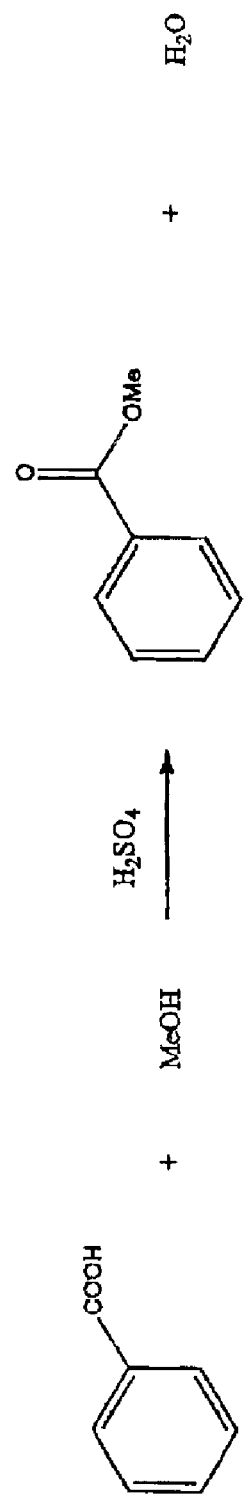

Table 4 shows the results of an esterification reaction (FIG. 13) between benzoic acid and butanol in the presence of sulfuric acid. The flow rate was set for 1.5 milliliter per minute in the 5-milliliter coil for a residence time of 3 minutes and 20 seconds. Using the cooling of the present invention, the temperature could be maintained at 80° centigrade while the power was maintained at 75 watts to give a yield of 100%. A comparable result from the prior art showed a 92% yield; e.g. U.S. Pat. No.

TABLE 5

| Transesterification Invention |
| --- |
| 30 mL BuOH |
| 0.4 mL H2SO4 |
| FR = 2 ml/min |
| 5 ml coil |
| Temp = 80 C. |
| P = 250 psi |
| Power = 100 W |
| Cooling = 1–2 psi |
| Yield = 89% |
| comparable results (No. 5,387,397) |
| 40% - 1st pass |
| 48% - 2nd pass |

Figure 14:
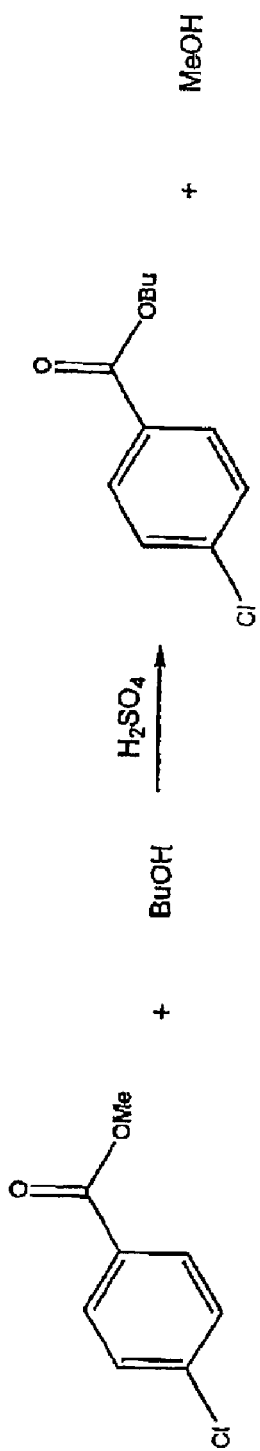

Table 5 shows the results for a transesterification reaction (FIG. 14) between methyl 4-chlorodenzoate and butanol also in the presence of sulfuric acid. The flow rate was 2 milliliter per minute in a 5-milliliter core for a residence time of 2½ minutes. Once again, the cooling step of the present invention enabled the temperature to be maintained at 80° C. while the power was applied at 100 watts. This produced an 89% yield of product comparable to yields of 40 and 48% in the prior art.

TABLE 6

| Nucleophilic Aromatic Substitution | |
| --- | --- |
| Invention | DISCOVER ™ Instrument |
| 6 g 4-chlorobenzaldehyde | 0.1 g 4-chlorobenzaldehyde |
| 4.4 mL isopropyl amine | 0.073 mL isopropyl amine, neat |
| 30 mL acetonitrile | |
| FR = 1.5 ml/min | |
| 5 ml coil | |
| residence time = 3:20 | 5 min ramp, 10 min hold |
| Temp = 90 C. | Temp = 175 C. |
| P = 250 psi | P = 250 psi |
| Power = 300 W | Power = 100 W to 300 W |

TABLE 6-continued

| Nucleophilic Aromatic Substitution | |
| --- | --- |
| Invention | DISCOVER ™ Instrument |
| Cooling = 10–13 psi | Cooling = On |
| Yield = 100% | Yield = 100% |

Figure 15:
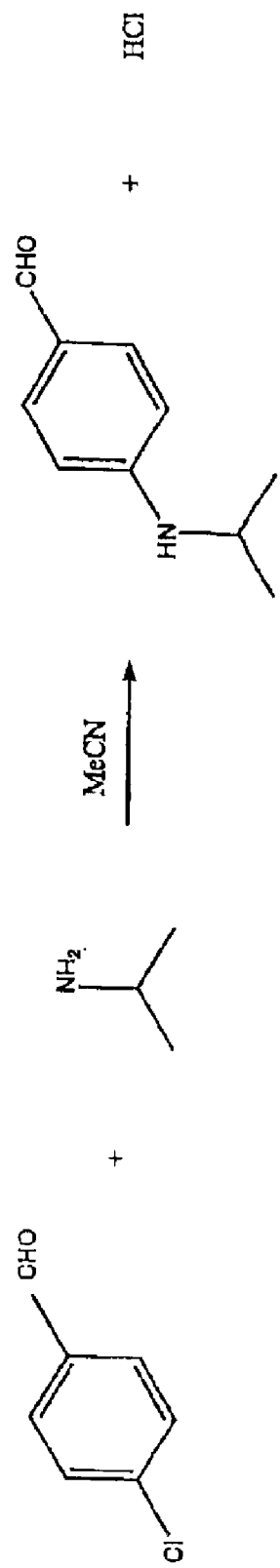

Table 6 shows a nucleophilic aromatic substitution reaction (FIG. 15). Table 6 demonstrates the comparison between the flow through technique of the present invention and the batch technique of the '261 application using the DISCOVER™ instrument. In Table 6, the reaction times differed slightly in that the method of the invention was carried out at a 1.5-milliliter flow rate in a 5-milliliter coil to produce a residence time of 3 minutes and 20 seconds, while in the batch reaction the reaction was allowed to run for 10 minutes. In each case, proactive cooling was applied so that the power level could be maintained between 100 and 300 watts. In each case, the yield was 100%.

TABLE 7

| Diels-Alder Invention | DISCOVER ™ Instrument |
| --- | --- |
| 6.8 mL furan | 0.107 mL furan |
| 15 mL diethylacetylene dicarboxylate neat | |
| FR = 0.5 ml/min | |
| 5 ml coil | |
| residence time = 10:00 | 10 min hold |
| Temp = 100 C. | Temp = 100 C. |
| P = 250 psi | P = 200 psi |
| Power = 300 W | Power = 300 W |
| Cooling 6–8 psi | Cooling = On |
| Yield = 92% | Yield = 85% |

Figure 16:
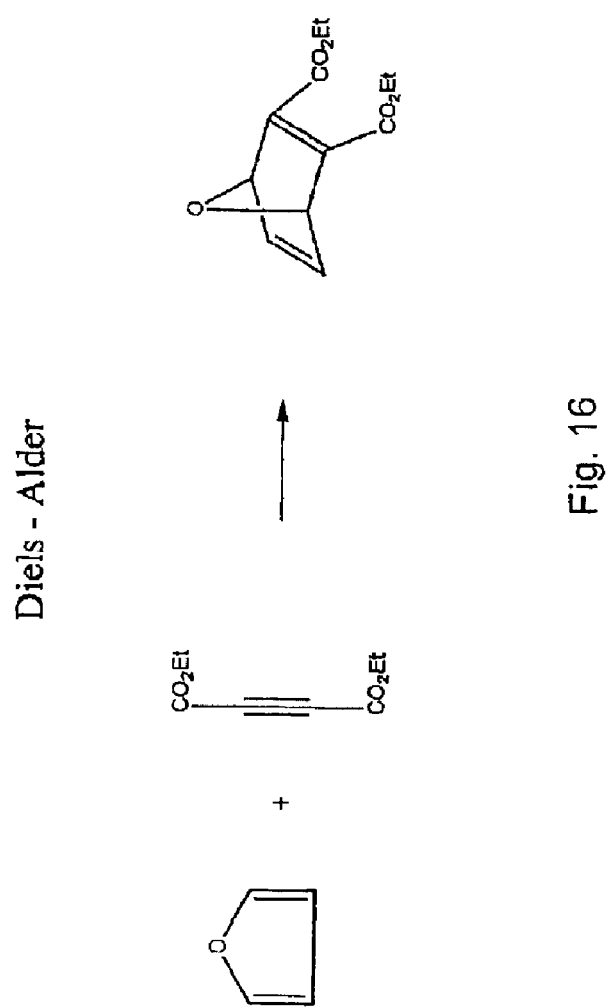

Table 7 shows the results of a Diels-Alder reaction (FIG. 16) and again comparing the flow through method of the present invention with the batch technique of the 261 application. In each case, the residence time was 10 minutes, with cooling applied to keep the temperature at 100° C., thus allowing power of 300 watts to be applied. The flow through technique of the invention showed a slightly greater yield of 92% as compared to the batch yield of 85%.

In the drawings and specification there has been set forth a preferred embodiment of the invention, and although specific terms have been employed, they are used in a generic and descriptive sense only and not for purposes of limitation, the scope of the invention being defined in the claims.

What is claimed is:

1. A method of microwave assisted chemistry comprising:
   directing a continuous flow of fluid through a single mode microwave cavity while applying microwave radiation to the cavity and to the continuous flow of materials therein;
   directing the fluid from the cavity to a spectroscopic flow cell and spectroscopically evaluating the fluid; and
   moderating the conditions in the cavity in response to the spectroscopic evaluation.

2. A method according to claim 1 wherein the step of directing the fluid to a spectroscopic flow cell comprises directing the fluid to a sample line and spectroscopically evaluating the fluid in the sample line.

3. A method according to claim 1 or claim 2 wherein the spectroscopy is selected from the group consisting of ultraviolet, infrared and Raman spectroscopy.

4. A method according to claim 1 wherein the step of moderating the cavity conditions comprises cooling the fluid flow in the cavity.

5. A method according to claim 1 wherein the step of moderating the cavity conditions comprises adjusting the fluid flow rate through the cavity.

6. A method according to claim 1 wherein the step of moderating the cavity conditions comprises moderating the microwave power applied in the cavity.

7. An instrument for microwave assisted chemistry comprising:
- a microwave cavity;
- a flow cell in said cavity;
- a spectroscopy cell external to said cavity and in fluid communication with said flow cell;
- a spectrometer with said spectroscopy cell in the optical path of said spectrometer for analyzing the characteristics of fluids flowing from said flow cell and through said spectroscopy cell; and
- a system for moderating conditions in the cavity in response to spectroscopic analysis by said spectrometer of fluids flowing from said flow cell and through said spectroscopy cell.

8. An instrument according to claim 7 comprising a pump in fluid communication with said flow cell for directing fluids from a source and into said flow cell in said cavity.

9. An instrument according to claim 7 and further comprising a system for cooling said flow cell in said cavity during the application of microwaves to said cavity.

10. An instrument according to claim 9 and further comprising a processor in signal communication with said spectrometer and with said cooling system.

11. An instrument according to claim 10 comprising a microwave source in microwave communication with said cavity and in signal communication with said processor; said microwave source being selected from the group consisting of magnetrons, klystrons and solid state devices.

12. An instrument according to claim 11 comprising a pressure detector in fluid communication with said flow cell and in signal communication with said processor.

13. An instrument according to claim 11 comprising a temperature detector in said cavity and in signal communication with said processor.

14. An instrument according to claim 11 comprising a waveguide between said source and said cavity and in microwave communication with said source and said cavity.

15. An instrument according to claim 7 comprising a single mode cavity.

16. An instrument according to claim 7 wherein said spectrometer is selected from the group consisting of infrared spectrometers, ultraviolet spectrometers, and Raman spectrometers.

17. An instrument according to claim 7, wherein said spectrometer is an absorption spectrometer comprising a source for directing radiation through said fluids and a detector for detecting the radiation after the radiation passes through said fluids.

18. An instrument for microwave assisted chemistry comprising:
- a microwave cavity;
- an attenuator releasably engaged with said cavity and in microwave communication with said cavity;
- a flow cell releasably engaged with said attenuator in a manner that fixes the positions of said attenuator and said flow cell with respect to one another when they are engaged and that correspondingly fixes said flow cell in the same position with respect to said cavity when said attenuator is engaged with said cavity.

* * * * *